(12) United States Patent
Gibson

(10) Patent No.: US 9,089,450 B2
(45) Date of Patent: Jul. 28, 2015

(54) IMPLANTABLE COMPONENT HAVING AN ACCESSIBLE LUMEN AND A DRUG RELEASE CAPSULE FOR INTRODUCTION INTO SAME

(75) Inventor: Peter Gibson, South Coogee (AU)

(73) Assignee: Cochlear Limited, Macquarie University, NSW (AU)

( * ) Notice: Subject to any disclaimer, the term of this patent is extended or adjusted under 35 U.S.C. 154(b) by 1252 days.

(21) Appl. No.: 12/248,889

(22) Filed: Oct. 9, 2008

(65) Prior Publication Data
US 2009/0076581 A1 Mar. 19, 2009

Related U.S. Application Data

(63) Continuation-in-part of application No. 10/416,634, filed as application No. PCT/AU01/01479 on Nov. 14, 2001, now Pat. No. 7,571,012.

(60) Provisional application No. 60/978,572, filed on Oct. 9, 2007.

(30) Foreign Application Priority Data

Nov. 14, 2000 (AU) .................................... PR1484

(51) Int. Cl.
*A61F 2/18* (2006.01)
*A61N 1/04* (2006.01)
(Continued)

(52) U.S. Cl.
CPC ............ *A61F 11/00* (2013.01); *A61M 5/14244* (2013.01); *A61M 31/002* (2013.01); *A61N 1/0541* (2013.01); *H04R 25/606* (2013.01); *A61M 5/14276* (2013.01);
(Continued)

(58) Field of Classification Search
CPC ............ A61M 25/00; A61M 5/14276; A61M 31/002; A61M 2210/0668; A61M 5/14244; A61M 2210/0662; A61M 2210/0675; A61N 1/0541; A61N 1/36032; A61F 11/00; H04R 25/606
USPC .......................... 607/3, 55–57, 120, 136–137
See application file for complete search history.

(56) References Cited

U.S. PATENT DOCUMENTS 3,890,977 A 6/1975 Wilson
4,046,151 A 9/1977 Rose
(Continued)

FOREIGN PATENT DOCUMENTS

AU EU 0007157 1/1980
AU EU 0706807 4/1996
(Continued)

OTHER PUBLICATIONS

Notice of Reason(s) for Rejection, related to Japanese Patent Application No. P2002-543261, Jan. 9, 2007.
(Continued)

*Primary Examiner* — Carl H Layno
*Assistant Examiner* — Erin Piateski

(57) ABSTRACT

A method for delivering drugs from an implantable medical device to an implantee, comprising implanting the medical device having a receptacle configured to receive a drug release capsule, the drug release capsule having at least one drug disposed thereon, placing the drug release capsule in the receptacle subsequent to the implanting, and permitting the release of the at least one drug from the drug release capsule to the recipient.

26 Claims, 8 Drawing Sheets

(51) Int. Cl.
  *A61F 11/00* (2006.01)
  *A61M 5/142* (2006.01)
  *A61M 31/00* (2006.01)
  *A61N 1/05* (2006.01)
  *H04R 25/00* (2006.01)
  *A61M 25/00* (2006.01)
  *A61N 1/36* (2006.01)

(52) U.S. Cl.
  CPC ....... *A61M 25/00* (2013.01); *A61M 2210/0662* (2013.01); *A61M 2210/0668* (2013.01); *A61M 2210/0675* (2013.01); *A61N 1/36032* (2013.01)

(56) References Cited

U.S. PATENT DOCUMENTS

| | | |
|---|---|---|
| 4,154,247 A | 5/1979 | O'Neill |
| 4,306,563 A | 12/1981 | Iwatschenko |
| 4,351,337 A | 9/1982 | Sidman |
| 4,357,479 A | 11/1982 | Imai |
| 4,381,013 A | 4/1983 | Dutcher |
| 4,506,680 A | 3/1985 | Stokes |
| 4,532,930 A | 8/1985 | Crosby et al. |
| 4,762,135 A | 8/1988 | van der Puije et al. |
| 4,784,161 A | 11/1988 | Skalsky et al. |
| 4,819,662 A | 4/1989 | Heil, Jr. et al. |
| 4,844,099 A | 7/1989 | Skalsky et al. |
| 4,972,848 A | 11/1990 | Di Domenico et al. |
| 4,994,069 A | 2/1991 | Ritchart et al. |
| 5,066,278 A | 11/1991 | Hirschberg et al. |
| 5,092,332 A | 3/1992 | Lee et al. |
| 5,265,608 A | 11/1993 | Lee et al. |
| 5,458,631 A | 10/1995 | Xavier |
| 5,474,542 A | 12/1995 | Ghandi et al. |
| 5,531,780 A | 7/1996 | Vachon |
| 5,538,504 A | 7/1996 | Linden et al. |
| 5,554,114 A | 9/1996 | Wallace et al. |
| 5,645,585 A | 7/1997 | Kuzma |
| 5,653,742 A | 8/1997 | Parker et al. |
| 5,697,951 A | 12/1997 | Harpstead et al. |
| 5,755,474 A | 5/1998 | Slomski |
| 5,755,765 A | 5/1998 | Hyde et al. |
| 5,769,077 A | 6/1998 | Lindegren |
| 5,782,744 A | 7/1998 | Money |
| 5,800,500 A | 9/1998 | Spelman et al. |
| 5,902,329 A | 5/1999 | Hoffmann et al. |
| 5,929,041 A | 7/1999 | Magal |
| 5,975,085 A | 11/1999 | Rise |
| 6,038,482 A | 3/2000 | Vachon |
| 6,038,483 A | 3/2000 | KenKnight et al. |
| 6,038,484 A | 3/2000 | Kuzma |
| 6,078,841 A | 6/2000 | Kuzma |
| 6,119,044 A | 9/2000 | Kuzma |
| 6,125,302 A | 9/2000 | Kuzma |
| 6,163,729 A | 12/2000 | Kuzma |
| 6,259,951 B1 | 7/2001 | Kuzma et al. |
| 6,304,787 B1 | 10/2001 | Kuzma et al. |
| 6,309,410 B1 | 10/2001 | Kuzma et al. |
| 6,321,125 B1 | 11/2001 | Kuzma |
| 6,398,758 B1 | 6/2002 | Jacobson et al. |
| 6,421,569 B1 | 7/2002 | Treaba et al. |
| 6,936,040 B2 | 8/2005 | Kramm et al. |
| 7,044,942 B2 | 5/2006 | Jolly et al. |
| 7,206,639 B2 | 4/2007 | Jacobsen et al. |
| 7,272,449 B2 | 9/2007 | Dadd et al. |
| 7,571,012 B2 | 8/2009 | Gibson |
| 8,133,215 B2 | 3/2012 | Gibson |
| 8,190,271 B2 * | 5/2012 | Overstreet et al. ............ 607/137 |
| 8,401,674 B2 | 3/2013 | Gibson |
| 2002/0032477 A1 | 3/2002 | Helmus et al. |
| 2002/0077685 A1 | 6/2002 | Sundquist et al. |
| 2003/0045921 A1 | 3/2003 | Dadd et al. |
| 2003/0097121 A1 | 5/2003 | Jolly et al. |
| 2003/0181967 A1 | 9/2003 | Dadd et al. |
| 2004/0030376 A1 | 2/2004 | Gibson et al. |
| 2004/0078057 A1 | 4/2004 | Gibson |
| 2004/0116995 A1 | 6/2004 | Dadd |
| 2004/0122501 A1 | 6/2004 | Dadd et al. |
| 2005/0177118 A1 | 8/2005 | Hoganson et al. |
| 2005/0256560 A1 | 11/2005 | Lenarz et al. |
| 2006/0287689 A1 | 12/2006 | Debruyne et al. |
| 2007/0184085 A1 | 8/2007 | Radhakrishnan et al. |
| 2008/0033520 A1 | 2/2008 | Jolly |
| 2009/0048580 A1 | 2/2009 | Gibson |
| 2009/0062896 A1 | 3/2009 | Overstreet et al. |
| 2009/0292237 A1 | 11/2009 | Overstreet et al. |
| 2011/0288468 A1 | 11/2011 | Dadd et al. |
| 2011/0288500 A1 | 11/2011 | Dadd et al. |

FOREIGN PATENT DOCUMENTS

| | | |
|---|---|---|
| DE | 10032000 | 1/2001 |
| EP | 0002068 | 5/1979 |
| EP | 0350188 | 1/1990 |
| EP | 0602859 | 6/1994 |
| EP | 0653223 | 5/1995 |
| EP | 0739642 | 10/1996 |
| EP | 0773037 | 5/1997 |
| EP | 0778043 | 6/1997 |
| EP | 0778044 | 6/1997 |
| EP | 0783900 | 7/1997 |
| EP | 0784994 | 7/1997 |
| EP | 0784995 | 7/1997 |
| EP | 0919254 | 6/1999 |
| EP | 0783901 | 4/2003 |
| EP | 1604626 | 12/2005 |
| EP | 2047884 | 4/2009 |
| GB | 2217993 | 11/1989 |
| JP | 55-190 | 5/1980 |
| JP | 8-229 137 | 9/1996 |
| JP | 9-508054 | 9/1997 |
| JP | 11-514252 | 11/1999 |
| WO | WO 96/15665 | 5/1996 |
| WO | WO 97/10784 | 3/1997 |
| WO | WO 99/00067 | 1/1999 |
| WO | WO 99/11321 | 3/1999 |
| WO | WO 99/55360 | 11/1999 |
| WO | WO 00/56399 | 9/2000 |
| WO | WO 00/57949 | 10/2000 |
| WO | WO 00/71063 | 11/2000 |
| WO | WO 01/41674 | 6/2001 |
| WO | WO 02/32498 | 4/2002 |
| WO | WO 02/41666 | 5/2002 |
| WO | WO 02/055136 | 7/2002 |
| WO | WO 02/082234 | 10/2002 |
| WO | WO 03/049658 | 6/2003 |
| WO | WO 03/072193 | 9/2003 |
| WO | 2009/067764 | 6/2009 |
| WO | WO 2009/124041 | 10/2009 |
| WO | WO 2010/045432 | 4/2010 |
| WO | 2011/148316 | 12/2011 |
| WO | 2011/148317 | 12/2011 |

OTHER PUBLICATIONS

Australian Examination Report related to Patent Application No. 2002223270. Dated Aug. 17, 2006.
Canadian Examination Report related to Patent Application No. 2,428,542, May 15, 2009.
European Examination Report dated Apr. 20, 2007, related to Application No. 01994538.5; Applicant Cochlear Limited.
International Search Report dated Nov. 29, 2001; corresponding PCT/AU01/01479, filed Dec. 2, 2001 published as WO 2002/4166 on May 23, 2002; Applicant Cochlear Limited; Inventor: Peter Gibson.
Written Opinion dated Jan. 28, 20021; corresponding PCT/AU01/01479, filed Dec. 2, 2001 published as WO 2002/4166 on May 23, 2002; Applicant Cochlear Limited; Inventor: Peter Gibson.
International Preliminary Examination Report dated Oct. 4, 2002; corresponding PCT/AU01/01479, filed Dec. 2, 2001 published as WO 2002/4166 on May 23, 2002; Applicant Cochlear Limited; Inventor: Peter Gibson.

(56) References Cited

OTHER PUBLICATIONS

Altschulere, et al., Rescue and Regrowth of Sendory Nerves Following Deafferentation by Neurotrophic factors, Annals New York Academy of Sciences.
Supplemental European Search Report. EP 01994538. Mailed May 27, 2005.
European Patent Office Extended Search Report for EP 08253298, dated Dec. 30, 2008.
Final Office Action for U.S. Appl. No. 12/535,374 mailed Jun. 21, 2010.
Non-Final Office Action for U.S. Appl. No. 10/416,634, mailed May 9, 2008.
Non-Final Office Action for U.S. Appl. No. 10/416,634, mailed Feb. 28, 2007.
Non-Final Office Action for U.S. Appl. No. 10/416,634, mailed Oct. 4, 2006.
Non-Final Office Action for U.S. Appl. No. 10/416,634, mailed Apr. 6, 2006.
Non-Final Office Action for U.S. Appl. No. 10/416,634, mailed Oct. 1, 2007.
Epicardial—Transvenous Left Ventricular Lead with Dual Ring Electrodes (Cathode Ring & Anode Ring) Design, Research Disclosure, Nov. 1997, 403-40349; pp. 790-791.
Epicardial—Transvenous Left Ventricular Lead with Wound Butterfly Electrode, Research Disclosure, Nov. 1997, 403-40342, p. 785.
European Patent Application No. 08253298.7, Office Action mailed on Nov. 6, 2009, 1 page.
European Patent Application No. 01973835.0, European Supplemental Search Report mailed on Jan. 22, 2004, 3 pages.
European Patent Application No. 08253298.7, Search Report mailed on Jan. 14, 2009, 5 Pages.
European Patent Application No. 08253298.7, Office Action mailed on Jul. 14, 2010, 2 pages.
International Application No. PCT/AU2001/01230, International Preliminary Examination Report mailed on Nov. 27, 2001, 3 pages.
International Application No. PCT/AU2001/01230, International Search Report mailed on Oct. 26, 2001, 3 Pages.
International Application No. PCT/AU2001/01231, International Search Report mailed on Oct. 26, 2001, 3 Pages.
International Application No. PCT/AU2001/01232, International Preliminary Examination Report mailed on Feb. 25, 2002, 3 Pages.
International Application No. PCT/AU2001/01232, International Search Report mailed on Oct. 26, 2001, 2 Pages.
International Application No. PCT/182011/052261, International Search Report mailed on Feb. 29, 2012, 3 Pages.
International Application No. PCT/182011/052261, Written Opinion mailed on Feb. 29, 2012, 4 Pages.
International Application No. PCT/182011/052262, International Search Report mailed on Feb. 29, 2012, 3 Pages.
International Application No. PCT/182011/052262, Written Opinion mailed on Feb. 29, 2012, 4 Pages.
PR 0541, Australian Search Report mailed on Dec. 20, 2000.
PR 0542, Australian Search Report mailed on Dec. 20, 2000.
PR 0684, Australian Search Report mailed on Dec. 20, 2000.
PR 0807, Australian Search Report mailed on Dec. 20, 2000.
PR 1005, Australian Search Report mailed on Dec. 20, 2000.
Examination Report in counterpart European Application No. 08253298.7, mailed Mar. 6, 2015, 3 pages.

* cited by examiner

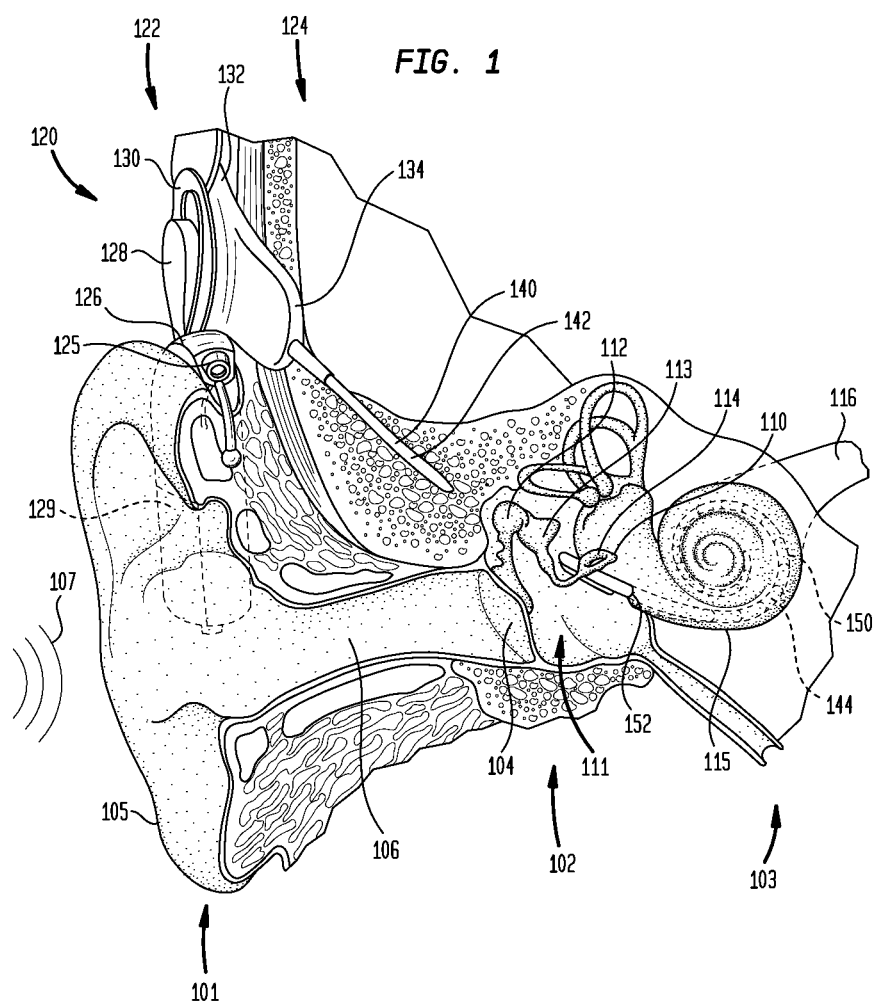

IMPLANTABLE COMPONENT HAVING AN ACCESSIBLE LUMEN AND A DRUG RELEASE CAPSULE FOR INTRODUCTION INTO SAME

CROSS-REFERENCE TO RELATED APPLICATIONS

This application is a Continuation-In-Part Application of application Ser. No. 10/416,634, filed on Nov. 10, 2003, issued on Aug. 4, 2009 as U.S. Pat. No. 7,571,012, entitled "Apparatus For Delivery of Pharmaceuticals To The Cochlear", which is a National Phase Application of International Application No. PCT/AU01/01479, filed Nov. 14, 2001, entitled "Apparatus For Delivery of Pharmaceuticals To The Cochlear", which claims priority from Australian Provisional Application No. PR 1484, filed Nov. 14, 2000. This application also claims priority from U.S. Provisional Patent Application No. 60/978,572, filed Oct. 9, 2007, entitled "Drug release Capsule For Implantation Into An Accessible Lumen Of An Implanted Medical Device. The above applications are hereby incorporated by reference herein.

BACKGROUND

1. Field of the Invention

The present invention relates generally to implantable medical devices, and more particularly, to a drug release capsule for implantation into an accessible lumen of an implantable medical device.

2. Related Art

Medical devices having one or more partially or completely implantable components, generally referred to as implantable medical devices, have provided a wide range of therapeutic benefits to patients over recent decades. One type of implantable medical device that has provided substantial benefits to patients over the years is a prosthetic hearing device. Prosthetic hearing devices process ambient sound to provide hearing ability to a hearing impaired patient.

Prosthetic hearing devices include a category of implantable devices known as cochlear™ implants (also referred to as cochlear™ devices, cochlear™ implant devices, and the like; "cochlear implants" herein). (COCHLEAR is a trademark of Cochlear Limited, Lane Cove, NSW, Australia.) Cochlear implants include an array of stimulation electrodes which is implanted in the cochlea of the patient (referred to herein as a recipient). The electrode array is controlled by an electronic system encased in a hermetically sealed, biocompatible housing implanted in the recipient. The electronic system, commonly referred to as a stimulator unit, essentially contains decoder and driver circuits for the stimulation electrodes. Acoustic sound reception and conversion of acoustic signals into electrical signals typically occurs in a sound processor typically worn by the recipient. The sound processor superimposes the preprocessed signals, properly coded, on a high frequency carrier signal which is transmitted transcutaneously to the stimulator unit through the closed skin. A sound input device such as a microphone converts ambient sound into representative electrical signals for processing by the sound processor. The sound input device is typically located outside of the recipient's body such as in a behind-the-ear housing worn on the auricle.

Traditionally, there has been interest in delivering a bioactive substance, pharmaceutical or chemical (collectively and generally referred to as a "drug" herein) in conjunction with implantable medical devices for a variety of purposes. For example, in one conventional approach an implantable medical device is coated with a drug. This and other conventional approaches typically require the incorporation of the drug into the implantable medical device during the manufacturing process of the device.

SUMMARY

In accordance with one aspect of the present invention, a drug delivery system comprising: an implanted component having an accessible lumen and one or more drug release ports fluidically coupling the lumen with an exterior environment of the implanted component; and a drug-delivery capsule that carries at least one drug and is configured to release the at least one drug, wherein the capsule and lumen are correspondingly configured such that the capsule may be introduced into the lumen so that when the drug-delivery capsule releases the at least one drug, the at least one drug may travel through the lumen and exit the implantable component via at least one of the one or more drug release ports.

BRIEF DESCRIPTION OF THE DRAWINGS

Illustrative embodiments of the present invention are described herein with reference to the accompanying drawings, in which:

FIG. 1 is a perspective view of an exemplary implantable medical device, a cochlear implant, in which embodiments of the drug release system of the present invention may be advantageously implemented;

DETAILED DESCRIPTION

Figure 2A:
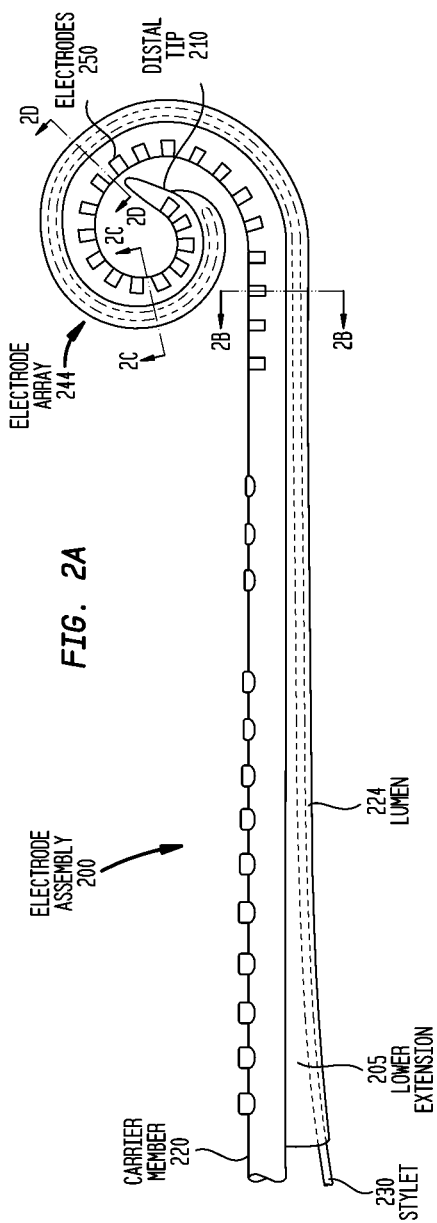
FIG. 2A is a side view of an embodiment of the electrode assembly illustrated in FIG. 1, in accordance with embodiments of the present invention.

Aspects of the present invention are generally directed to a drug delivery system for delivering a drug in connection with an implanted component having an accessible lumen. The implantable component may be a component of an implantable medical device. For example, the component may be a cochlear implant electrode assembly that has a lumen for receiving a stylet. In addition to the lumen of the implantable component, the drug release system comprises a drug release capsule that carries a drug. The capsule and lumen are correspondingly configured such that the capsule may be introduced into the lumen, advanced to a desired position in the lumen, and securely retained within the lumen. Because the implantable component and the drug release capsule are physically distinct, the component and capsule may be independently-manufactured, and the drug release capsule may be joined with the implantable component subsequent to the device's manufacture and/or sterilization of the component, and prior to, concurrently with, or subsequent to the implantation of the implantable medical device component.

Manufacturing a drug release capsule separately from the implantable medical device component provides flexibility in the applied therapy while reducing the undesirable aspects associated with integrating drugs in implantable medical devices. For example, embodiments of the present invention may enable manufacturing efforts to be focused solely on the successful manufacture of the medical device component rather than on manufacturing an integrated assembly of the component and drug-delivery mechanism. This may result in reduced manufacturing costs, reduced drug yield loss, reduced handling and contamination of drugs, and other benefits. Furthermore, this may allow for the manufacturing of the drug release capsule to be outsourced to specialist manufacturers. Such outsourcing may provide further benefits such as the reduction of the cost of research and development by outsourcing to manufacturers that already have regulatory approval for the desired drugs, thus allowing faster and better provision of the medical devices incorporating the drug release capsules to the relevant market. Additionally, by manufacturing the drug release capsule separately from the device itself, the implantable medical device may be utilized as a universal device having a standardized lumen that may be loaded with different embodiments of the drug release capsules. This advantageously enables a single implantable device to be manufactured and inventoried without being restricted to operating with a single drug or specific combination or dosage of drugs. This is particularly advantageous in those circumstances in which the drug to be delivered via the drug release capsule has a limited shelf life.

As used herein, the term "drug" refers to any bioactive substance or chemical now or later developed, including, but not limited to, pharmaceuticals and other chemical compounds such as those intended to provide therapeutic benefits to, or other reactions in, an implant recipient, whether localized or distributed throughout the recipient. Such drugs may include, for example, steroids or other anti-inflammatory drugs to reduce inflammation at the implantation site. Other drugs that may be included in the drug release capsules are antibiotics to mitigate bacterial growth related to the implantation of the medical device component. It should be appreciated that as used herein the term "drug release capsule" refers to any mass of material suitable for carrying a desired one or more drugs for subsequent release into the recipient, and which is configured to be introduced into and securely positioned within a lumen of the implantable medical device component. The more common definition of a capsule in the field of pharmacology; that is, a gelatinous case enclosing a dose of medicine, is just one of a myriad of embodiments of the drug release capsule of the present invention. This is described in greater detail below.

FIG. 1 is a perspective view of an exemplary implantable medical device in which embodiments of a drug release system of the present invention may be implemented. In fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound. In certain profoundly deaf persons, there is an absence or destruction of the hair cells. Cochlear implants such a cochlear implant 120 is utilized to directly stimulate the ganglion cells to provide a hearing sensation to the recipient.

FIG. 1 also shows the positioning of cochlear implant 120 relative to outer ear 101, middle ear 102 and inner ear 103. Cochlear implant 120 comprises external component assembly 122 which is directly or indirectly attached to the body of the recipient, and an internal component assembly 124 which is temporarily or permanently implanted in the recipient. External assembly 122 comprises microphone 125 for detecting sound which is outputted to a behind-the-ear (BTE) speech processing unit 126 that generates coded signals which are provided to an external transmitter unit 128, along with power from a power source 129 such as a battery. External transmitter unit 128 comprises an external coil 130 and, preferably, a magnet (not shown) secured directly or indirectly in external coil 130.

Internal component assembly 124 comprise an internal coil 132 of a stimulator unit 134 that receives and transmits power and coded signals received from external assembly 122 to other elements of stimulator unit 134 which apply the coded signal to cochlea 115 via an implanted electrode assembly 140. Electrode assembly 140 enters cochlea 115 at cochleostomy region 152 and has one or more electrodes 150 positioned on an electrode array 144 to be substantially aligned with portions of tonotopically-mapped cochlea 115. Signals generated by stimulator unit 134 are typically applied by an array 144 of electrodes 150 to cochlea 115, thereby stimulating auditory nerve 116.

Given the coiled shape of cochlea 115, electrode carrier member 142 is typically constructed using a material, or combination of materials, which curls or is capable of being curled in a manner which follows the curvature of cochlea 115. The portion of electrode assembly 140 intended to be inserted into cochlea 115 will often have a stiffening stylet (not shown) inserted into a channel, for example a lumen (not shown), which extends distally from the proximate end of electrode carrier member 142. During implantation of electrode assembly 140, the stylet contained in the lumen of carrier member 142 is removed from the proximate end of the carrier member as the carrier member is inserted into cochlea 115. The act of removing the stiffening stylet from the lumen allows electrode carrier member 142 to curl. In further embodiments of cochlear implant 120, the stiffness of the stylet decreases in response to fluids and/or body temperature allowing electrode carrier member 142 to curl in order to follow the curvature of the inner walls of cochlea 115. In other embodiments of cochlear devices, electrode carrier member 142 is naturally straight without the assistance of a stylet inserted into the lumen. Such embodiments of electrode carrier member 142 are constructed using a flexible material, or is constructed so as to flex upon a fixed amount of force being exerted on the tip or body of electrode carrier member 142 as it is being inserted into cochlea 115.

As one of ordinary skill in the art will appreciate, embodiments of the present invention may be advantageously implemented in a variety of implantable components. In the exemplary application above of cochlear implant 120, the implantable component is electrode carrier member 142 which is permanently implanted in cochlea 115 of a recipient.

Figure 2B:
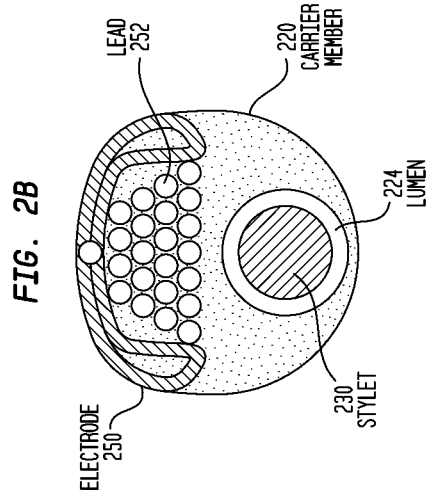
FIG. 2B is a cross-sectional view of the electrode assembly illustrated in FIG. 2A taken along section line 2B-2B in FIG. 2A.
Figure 2C:
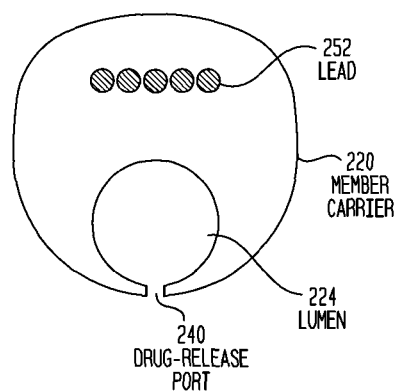
FIG. 2C is a cross-sectional view of the electrode assembly illustrated in FIG. 2A taken along section line 2C-2C in FIG. 2A.
Figure 2D:
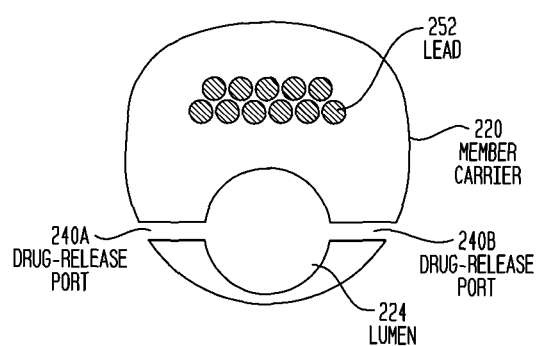
FIG. 2D is a cross-sectional view of the electrode assembly illustrated in FIG. 2A taken along section line 2D-2D in FIG. 2A.
Figure 3:
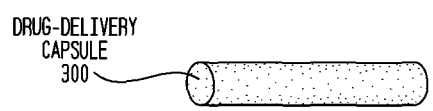
FIG. 3 is a perspective view of a drug delivery capsule in accordance with one embodiment of the present invention.

Embodiments of a drug release system of the present invention is described next below with reference to FIGS. 2A through 2D. FIG. 2A is a side view of an embodiment of electrode carrier member 142, referred to herein as electrode assembly 200. FIGS. 2B-2D are cross-sectional views of electrode assembly 200 taken along their respective cross-sectional lines shown in FIG. 2A. A perspective view of an exemplary embodiment of a drug-delivery capsule of the present invention is illustrated in FIG. 3.

Drug-delivery capsule 300 is substantially cylindrical in shape and is constructed and may take on any form to retain and release one or more drugs into lumen 224. In one embodiment, drug-delivery capsule 300 may be formed by impregnating the drug in a ceramic or a polymer material that is configured to release the drug at a predetermined rate.

Electrode assembly 200 comprises an elongate carrier member 220 on which an electrode array 244 of electrodes 250 is disposed. As noted, each electrode 250 is constructed and arranged to deliver a stimulating signal to a particular region of cochlea 115.

It has been found that the magnitude of the currents flowing from electrodes 250, and the intensity of the corresponding electric fields, are a function of the distance between electrodes 250 and the modiolus (not shown) of cochlea 115. If this distance is relatively great, the threshold current magnitude must be larger than if this distance is relatively small. Moreover, the current from each electrode 250 may flow in a number of directions, and the electrical fields corresponding to adjacent electrodes may overlap, thereby causing cross-electrode interference. To reduce such adverse effects, it is advisable to maintain a minimal distance between carrier member 220 and the modiolus. This is best accomplished by providing carrier member 220 in a shape which generally follows the shape of the modiolus, or inside wall of cochlea 115 (FIG. 1). This increases the effectiveness of the delivery of electrical stimulation to auditory nerve 116 (FIG. 1).

In this exemplary application, to position electrodes 250 adjacent the inside wall of cochlea 115, carrier member 220 adopts a curled or spiral position immediately following implantation into cochlea 115. It is also desirable that carrier member 220 be shaped such that the insertion process causes minimal trauma to the sensitive structures of cochlea 115. As such, carrier member 220 is manufactured to be pre-curved. Specifically, carrier member 220 is manufactured to have a spiral configuration; that is, one or more concentric circles that approximate the curvature of cochlea 115 as shown in FIG. 2A.

Usually carrier member 220 is held in a generally straight configuration at least during the initial stages of the insertion procedure, conforming to the natural shape of cochlea 115 once implantation is complete. To have carrier member 220 assume a generally straight configuration, a lumen 224 is provided in the carrier member. In the illustrative application of carrier member 220, lumen 224 extends through a substantial length of a lower extension 205 of carrier member 220.

Lumen 224 is configured to receive a stiffening element 230 commonly referred to in the context of prosthetic hearing implants as a stylet. Although such reference is used in connection with prosthetic hearing devices, it should be appreciated that the term "stylet" is not limiting to any particular application or configuration.

Prior to implanting carrier member 220, stylet 230 is inserted into lumen 224 to maintain the carrier member in a relatively straight configuration. While electrode assembly 200 is inserted through cochleostomy 152 (or the oval window of the cochlea, not shown), a surgeon biases forward carrier member 220 on stylet 230 to allow carrier member 220 to return to its spiral configuration and, in doing so, to follow the curvature of cochlea 115. In other words, during insertion, stylet 230 is withdrawn from lumen 224 thereby allowing carrier member 220 to return to its pre-curved configuration.

In one embodiment, the technique for implanting electrode assembly 200 is the Advance Off-Stylet™ technique for the Contour™ Advance electrode (previously referred to as the Contour™ Electrode with Softip). In a another embodiment, electrode assembly 200 includes a Contour™ Advance Electrode, also described as Contour™ Electrode with Softip, Modified Tip, or Ski Tip. In another embodiment, the stylet is an Arrow Stylet, Surgical Stylet, or Surgical Ball Stylet. In these and other stylets and electrode carrier members, the stylet is removably inserted into lumen 224 of the carrier member prior to implantation, and is removed from the carrier member during implantation.

FIGS. 2C and 2D are cross-sectional views of electrode assembly 200 taken along cross-sectional lines 2C-2C and 2D-2D in FIG. 2A. FIGS. 2C and 2D are schematic representations of two exemplary embodiments of drug release ports 240 which may be implemented in carrier member 220 to fluidically couple lumen 224 with an exterior environment of electrode assembly 200. In the illustrative application shown in FIG. 1, for example, such external environment is one of the ducts of cochlea 115. In the exemplary embodiments illustrated in FIGS. 2C and 2D, drug release ports 240 are in the form of a narrow channel or opening in carrier member 220. For example, in the embodiment illustrated in FIG. 2C, a drug release port 240 extends from lumen 224 with the exterior surface of carrier member 220 which opposes the side of carrier member 220 on which electrodes 250 are disposed. As such, drug release port 240 fluidically couples lumen 224 with the exterior environment of electrode assembly 200 toward the lateral wall of cochlea 115 when electrode assembly 200 is implanted in the cochlea. As another example, in the embodiment illustrated in FIG. 2D, two drug release ports 240A and 240B are formed in carrier member 220 on laterally-opposing sides of lumen 224. It should be appreciated that the location, configuration, dimensions, and quantity of drug release ports 240 may vary depending on the particular application, type, configuration and quantity of the drug-delivery capsule and other factors such as the rate at which the capsule releases the drug, the molecular characteristics of the drug, and so on.

Drug release ports 240 may be passageways or channels within carrier member 220 as shown in FIGS. 2C and 2D. It should be appreciated, however, that in other embodiments, drug release ports 240 are implemented as a permeable structure within a membrane which makes up at least a part of electrode carrier member within carrier member 220. Such drug release ports 240 allow drugs to move into cochlea 115 in the absence of a gross movement of fluid. In addition to permitting the flow of drugs into cochlea 115, drug release ports 240 may be configured to control the rate of drug flow into cochlea 115. In alternative embodiments, drug release ports 240 may be controllable. For example, in one specific embodiment, drug release ports 240 are responsive heat, adjusting the permeability in response to an applied heat source.

Figure 5A:
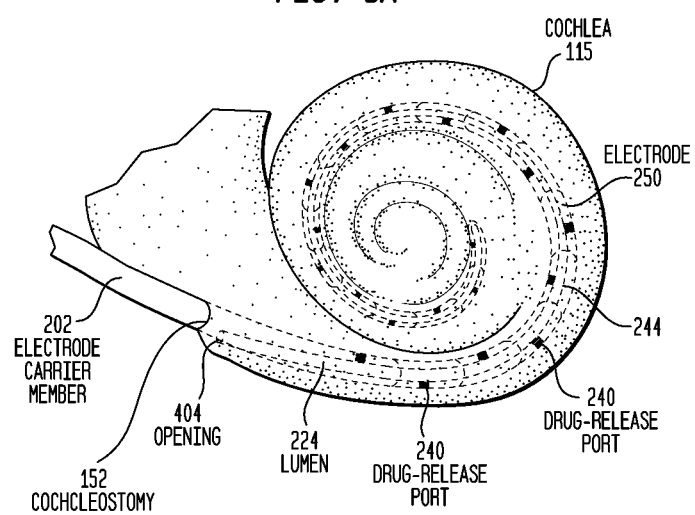
FIG. 5A is a partial view of the cochlea and an embodiment of the electrode assembly illustrated in FIG. 2A, in which the electrode assembly has a lumen with multiple portholes, in accordance with an embodiment of the present invention.
Figure 5B:
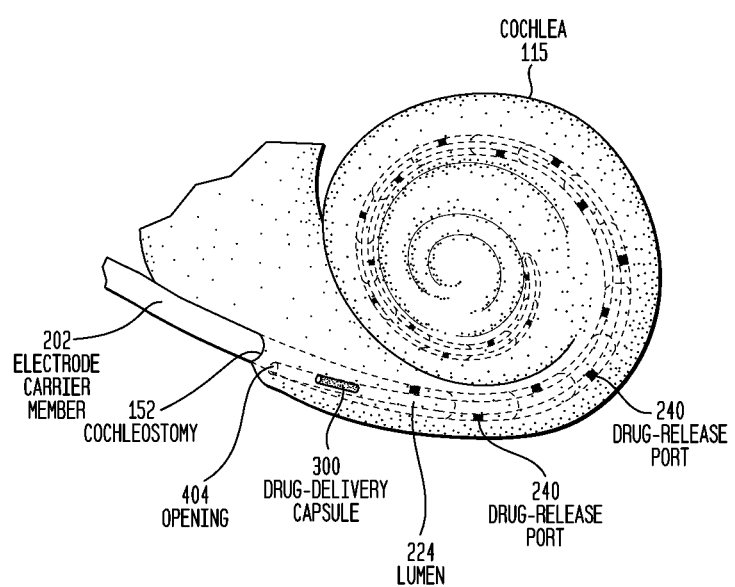
FIG. 5B is the perspective view of the electrode assembly of FIG. 2A with the drug release capsule of FIG. 3 positioned within the lumen, in accordance with one embodiment of the present invention.
Figure 5C:
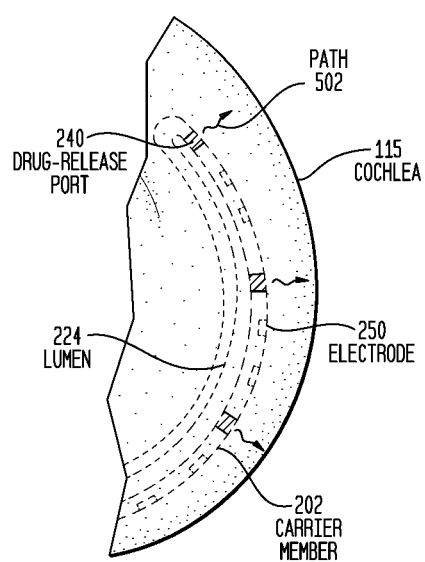
FIG. 5C is an enlarged view of the cochlea and electrode assembly of FIG. 5B showing the releasing of drugs through multiple portholes disposed on the electrode assembly.

FIG. 5A is a partial view of cochlea 115 implanted with an embodiment of electrode assembly 200 illustrated in FIG. 2A. in which the electrode assembly has a lumen with multiple portholes 240, in accordance with embodiments of the present invention. FIG. 5B is the same view of electrode assembly 200 shown in the same implanted position as in FIG. 5A with a drug release capsule 300 positioned within the lumen, in accordance with embodiments of the present invention. FIG. 5C is an enlarged view of cochlea 115 and electrode assembly 200 showing the release of drugs through multiple portholes 240 disposed on the electrode assembly.

In the exemplary embodiment of electrode assembly 200 illustrated in FIGS. 5A-5D, multiple portholes 240 are formed in carrier member 220 circumferentially around lumen 224, providing a passageway from lumen 224 to locations exterior of electrode assembly 200. It is to be understood, however, that drug delivery ports 240 may be disposed along any portion of the perimeter or circumference of electrode carrier member within carrier member 220.

Electrode assembly 200 is implanted in a recipient by inserting electrode carrier member within carrier member 220 through, for example, cochleostomy region 152 which is formed in a portion of the recipient's cochlea 115. Lumen 224, as noted, is manufactured as a hollow channel inside electrode carrier member within carrier member 220 and terminates at an opening 404 at or near cochleostomy region 152, inside cochlea 115. Lumen 224 is configured to receive and securely retain a correspondingly-configured drug release capsule 300 (FIG. 3) as shown in FIG. 2C.

Although lumen 224 is depicted in FIG. 5A as starting from a location which is inside cochlea 115 just beyond cochleostomy region 152, and which extends along a substantial length of electrode assembly 200, it is to be understood that lumen 224 may extend along electrode carrier member 220 starting from and ending at any point along electrode carrier member 220. For example, in one embodiment, lumen 224 extends along electrode assembly 200 from outside cochlea 115 to inside the cochlea when the device is implanted in the cochlea. As such, electrode carrier member 220 may be configured so that opening 404 for lumen 224 is located outside cochlea 115 when the carrier member is implanted in cochlea 115. In such an embodiment, a plug or other type of seal may be used to provide an impermeable obstruction to prevent cochlea fluids from leaking out of cochlea 115. It is also to be understood that electrode assembly 200 may be of various lengths and extend into cochlea 115 to different depths. It is also to be understood that although it is noted above that electrode carrier member 220 is preferably configured to be adjacent to the perimodiolar wall of cochlea 115 upon insertion, or may be configured to follow the lateral wall of cochlea 115.

As best illustrated in FIG. 2D, as drug release capsule 300 releases the drug it is carrying, the drug travels through lumen 224 and exists the lumen through one or more ports 240, as illustrated by arrows 502.

FIG. 2D also depicts a recess 208 configured to receive and securely retain a drug release capsule 300 inserted into lumen 224. Drug release capsule 300 is inserted inside lumen 224 of electrode carrier member 220 through opening 404 of lumen 224. As shown in FIG. 2D, a plurality of ports 240 are disposed in various regions of electrode carrier member 220 to provide a path of travel for bodily fluids (not shown), heat energy (not shown), and drugs disposed on drug release capsule 300 to travel between lumen 224 and inner areas of cochlea 115, indicated by arrows 2D in FIG. 2A. In one embodiment, drug release capsule 300 interacts with fluids present in cochlea 115, which enters lumen 224 through ports 240, to release drugs carrier by drug release capsule 300 into the fluids. The resulting fluid and drug mixture travels out of lumen 224 through ports 240 into cochlea 115. In addition to providing localized benefits to the recipient's cochlea, it is to be understood that the drugs carrier by drug release capsule 300 and released into the recipient in the manner described above may also provide general benefits or benefits to other parts of the recipient's body remote from cochlea 115.

Figure 4A:
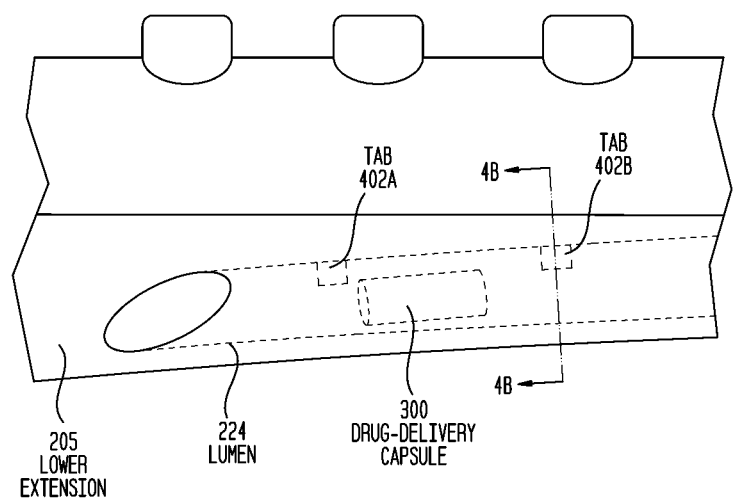
FIG. 4A is a partial view of an electrode assembly in which retention tabs provide an interference retention to maintain a drug release capsule in a desired location inside the lumen of the implantable medical device component.

As depicted in FIG. 4A, in some embodiments of the present invention, the interior walls of electrode carrier member 220 that define lumen 224 may have one or more tabs 402A, 402B configured to receive and securely retain drug release capsule 300 inserted into lumen 224. For example, in one embodiment, drug release capsule 300 is securely retained in the lumen between tabs 402 due to the respective dimensions of the tabs and capsule. Alternatively, drug release capsule 300 is securely retained in lumen 224 due to a compression fit. Alternatively, a recess, rough edges, and the link may be formed in lumen 224 to facilitate retaining capsule 300 in a desired position in lumen 224. In such embodiments the drugs carried by drug release capsule 300 interact with body fluids and/or temperature so that the drugs are carried out through various portholes 240. Inserting drug release capsules 300 so as to be positioned securely at a desired location within recesses 208 inside lumen 224 of electrode carrier member 220 may be beneficial for keeping lumen 24 free of any objects while allowing drugs to escape from lumen 224, through ports 240.

Figure 5D:
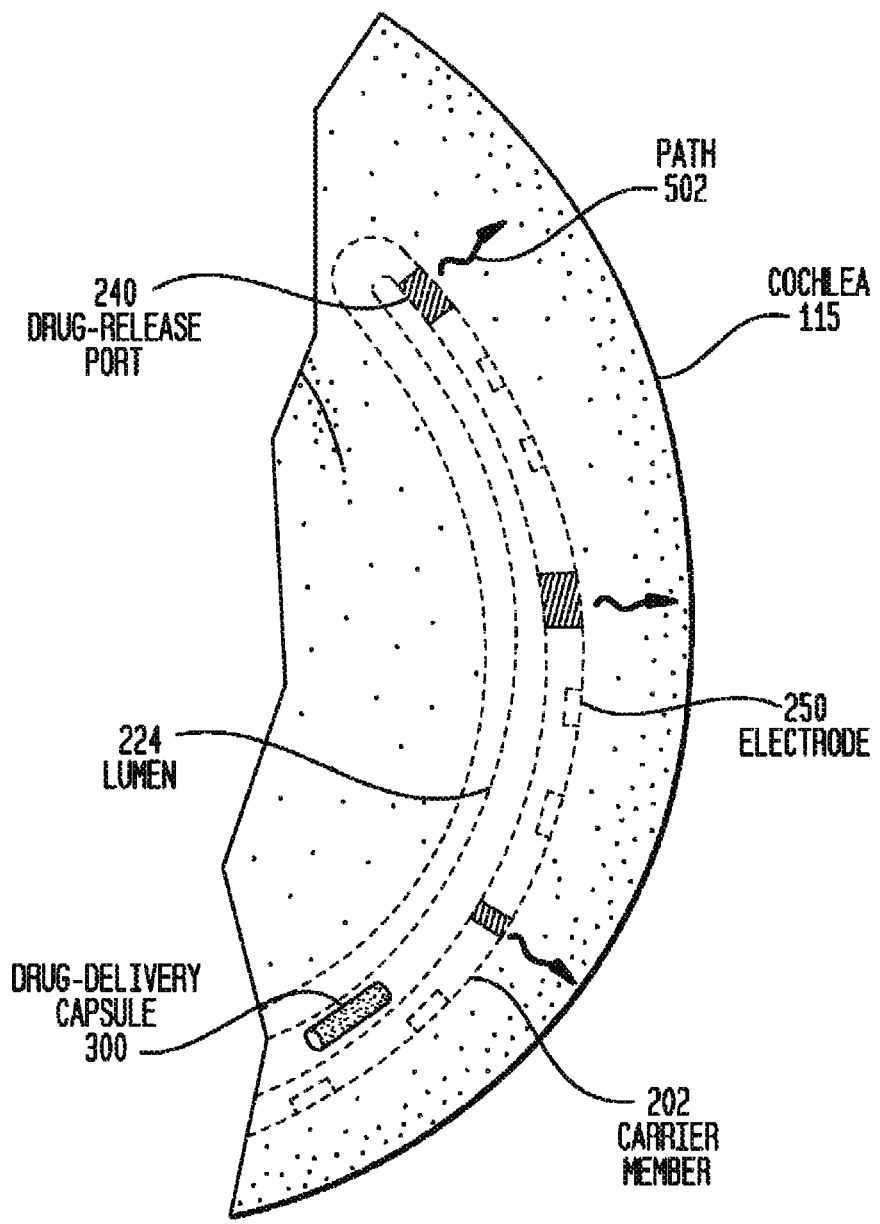
FIG. 5D is an enlarged view of the cochlea and electrode assembly of FIG. 5B showing the releasing of drugs through multiple portholes disposed on the electrode assembly.

In other embodiments of the present invention, ports 240 may be dimensioned and/or arranged along electrode carrier member 220 to attain a desired outcome with or without a specialized drug release capsule configuration. For example, ports 240 disposed closer to drug release capsule 300, when drug release capsule 300 is inserted into lumen 224, may be configured to be smaller than ports 240 that will be further from the implanted position of drug release capsule 300. Such a configuration may beneficially direct the same amount of drugs to escape from those ports 240 that are further away from drug release capsule 300 as would escape from ports 240 that are closer to drug release capsule 300. Alternatively, by dimensioning all portholes along electrode carrier member 220 to be of the same size, more drugs may be delivered to ports 240 that are nearer to drug release capsule 300 as compared to ports 240 that are further from drug release capsule 300. Additionally, ports 240 may generally be designed to be smaller in one embodiment of drug release system 200 than in other embodiments of the present invention for the purpose of reducing the amount of drugs released from drug release system 200, as described above. For example, as part of a miniaturization effort for making these implantable devices more sophisticated or smaller for better suited for implantation in a recipient, drug release capsule 300 is highly concentrated with the drugs disposed thereon. Depending on the amount or rate of discharge desired, portholes 204 may be configured to have larger or smaller openings, as shown in FIG. 5D, or to have thicker or thinner sidewall thicknesses, which will impact the rate, volume or type of interaction permitted between drug release capsule 300 and body fluids or heat energy, in order to achieve the desired amount or rate of discharge from drug release system 200.

Figure 4B:
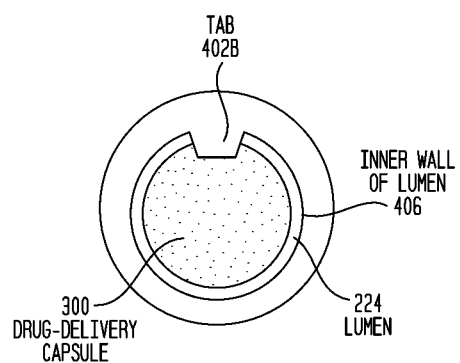
FIG. 4B is a cross-sectional view of the electrode assembly of FIG. 4A taken along section line 4B-4B, in accordance with embodiments of the present invention.

In certain embodiments of the present invention, drug release capsule 300 is maintained in place after being inserted into lumen 224 by retention tab 402, as shown in FIGS. 4A and 4B. FIG. 4A is a partial view of an embodiment in which retention tabs 402A and 402B maintain drug release capsule 300 in place inside electrode assembly 200. FIG. 4B is a cross-sectional view of electrode assembly 200 taken along section line 4B-4B showing retention tab 402B. Drug release capsule 300 is shown inserted through lumen opening 404 into lumen 224 of electrode assembly 200. Retention tab 402B projects inwardly into lumen 224 from electrode assembly 140 and prevents drug release capsule 300 from further entering lumen 224 by interfering with that path of travel. Retention tab 402B also projects inwardly into lumen 224 from electrode assembly 140 and prevents drug release capsule 300 from escaping out of electrode assembly 140 through lumen opening 404. Retention tabs 402A, 402B may be integrally formed with electrode assembly 140, or may be separately formed attached to electrode assembly, and may be resilient to some degree. Drug release capsule 300 is inserted into lumen 224 through lumen opening 205. During insertion, when sufficient force is applied to drug release capsule 300, resiliently formed interference tab 402B compresses or bends sufficiently to permit the continued insertion of drug release capsule 300 into lumen 224 towards interference tab 402A. When fully inserted, drug release capsule 300 may be positioned in lumen 224 aligned with either or both interference tabs 402A and 402B such that one or both are compressed by drug release capsule 300. Alternatively, interference tabs 402A and 402B may be positioned apart from one another such that drug release component 202 is situated between and apart from both interference tabs 402A and 402B.

Although an interference retention is described above with regard to FIGS. 4A and 4B, it is to be understood that other types of retention are possible to maintain the position of drug release capsule 300 when inserted into lumen 224. For example, a compression retention, bonded retention, sutures, screws, clips, a combination of the above, or others may be used for such a purpose. In a compression retention, drug release capsule 300 is manufactured to be resilient to some degree and slightly larger than lumen 224 along at least a portion of lumen 224. Alternatively, drug capsule 300 may be manufactured to be rigid and electrode assembly 140 having lumen 224 therein may be manufactured to be resilient to some degree. When inserted into lumen 224, drug release component 202 will compress, electrode assembly 140 will expand, or a combination of the two will occur, so that a compression force is created between drug release capsule 300 and electrode assembly 140, thereby securely retaining drug release capsule 300 in that position.

In another embodiment, the drug release capsule may be configured to be bonded into the corresponding lumen of the implantable medical device thereby eliminating the need for a non-bonded retention means (e.g., compression retention, interference retention) between the drug release capsule and the lumen of the medical device. In one embodiment, such bonding is performed in a sterile field immediately prior to surgery, for example by inserting a ring-shaped drug release capsule around a stylet that has yet to be removed from an electrode array. Alternatively, such bonding is performed after the medical device is implanted in the patient. In another embodiment, such bonding is performed during manufacturing, such as one of the last few steps of manufacturing.

In one embodiment, the above bonding is performed by disposing a glue layer on the lumen so that the drug release capsule may be pressed in prior to surgery. This may be performed manually or with a simple press-tool that aligns the two components and presses them together with a predefined amount of pressure. Alternatively, a liquid glue may be applied between the lumen surface and the drug release capsule. In one preferred embodiment, the liquid glue sets and/or cures rapidly. In another embodiment, a UV-cured glue is pre-applied to the component, or applied as a liquid, or is a separate component that is inserted between the drug release capsule and the lumen within the implantable medical device. In one embodiment, a liquid perfluoropol polymer such as that described in International Application WO 2007/021620 A2 may be utilized. International Application WO 2007/021620 A2 is hereby incorporated by reference herein. Other adhesives include, but are not limited to, fibrin glues, cyanoacrylates, polyurethane adhesives, silicone adhesives, and UC-cured acrylics. In another embodiment, chemical surface modification may be utilized to attain a desired bonding. For example, in one embodiment, covalently bonded proteins, or sulfonation may be performed to increase the wetability of the surface.

It may be desirable for embodiments of the drug release capsule of the present invention to be constructed of a resorbable material, so that while drugs are being absorbed from the lumen, or after they are absorbed, the drug release capsule may be partially or completely resorbed by the tissue surrounding the implant site. In certain embodiments, the drug release capsule is comprised of a resorbable material that partially or completely degrades over time through interaction with various body fluids. In other embodiments, the drug release capsule is comprised of a resorbable material that partially or completely degrades over time through exposure to body temperatures.

However, it may also be desirable for the drug release capsule to be constructed of a non-resorbable material. The use of a non-resorbable material may offer different benefits from the use of a resorbable material, such as the continued provision of a flush and gapless surface on one or more sides of the implantable medical device or tissue. For example, the drug release capsule may be made of a polymeric material configured to enable drugs to be embedded within the structure of the polymeric material, and to release the drugs either naturally or through the interaction of body fluids or body heat which may permeate the capsule. Furthermore, the drug release capsule may have micro-surface geometry, such as those possible through advances in nano-technologies, which may limit or inhibit bacteria growth.

It should also be appreciated that the drug release capsules described above may be formed by one or more layers or sub-parts. In other words, each drug release capsule may be a composite of multiple layers or sub-parts. Each such layer or sub-part may serve a different function, for example, being configured to carry a different drug, releasing the same or different drug at the same or different rate, or having different concentrations of a drug across one or more portions of the drug release capsule.

Furthermore, it is to be understood that drugs may be disposed on just a portion of a drug release capsule depending on the particular application. For example, it may be beneficial for a drug release capsule to have a drug disposed on only a portion of the capsule, with the remaining portion of the capsule configured merely as a carrier or supporting member for the medicated portion of the drug release capsule.

According to a further embodiment of the present invention, the drug release capsule may be constructed of a polymeric material, in which molecules or other components of a drug are disposed within the chemical structure of the drug release capsule. One example of a polymeric material which may be used to construct an embodiment of a drug release capsule of the present invention is silicone. Drugs may be disposed within the silicone drug release capsule such that the drug is released from the drug release capsule.

According to another embodiment of the present invention, the surface of the drug release capsule may be constructed to have microsurface geometry. Such a microsurface geometry may be constructed using nano-technologies, or may be constructed using other technologies presently known or developed in the future. Having a microsurface geometry may enable the drug release capsule to be useful in partially or completely inhibiting growth of bacteria and other biological organisms adjacent to the drug release capsule.

According to yet another embodiment of the present invention, drug release capsule 300 may be formed to be resilient to some degree, for use in situations where it is desirable to insert a soft or flexible capsule into an implanted medical device. For example, where the medical device a cochlear implant comprising electrode array 144, it may be desirable to advance drug release capsule 300 past the first curved portion inside cochlea 115. In that case, having a resilient capsule 300 may be useful or even necessary for such an insertion such that the outer shape of electrode array 144 is not deformed or otherwise unacceptably altered so as to negatively impact the operation or durability of the electrode array 144 and surrounding anatomy.

Conversely, drug release capsule 300 may be formed as a rigid capsule and used to provide or supplement the structural integrity of lumen 224. For example, rigid drug release capsule 300 having a straight or other shape may be inserted into lumen 224 so that drug release capsule 300 provides or reinforces the shape of electrode array 144 surrounding lumen 224 through rigid drug release capsule 300.

Although various embodiments of the present invention have been described herein as a single capsule, it is to be understood that embodiments in which the drug release capsule 202 comprise multiple components, some of which may be drug release capsules and some of which may serve other functions, are also considered a part of the present invention. Examples include, but are not limited to, a drug release capsule component carrying drugs which promote tissue growth, for example to promote, cause or support the sealing of the cochleostomy region 152 or oval window 110. Another example is a drug release capsule component carrying drugs which promote enhanced stimulation. These and other components may be inserted into lumen 224 of electrode array 144 as described above. Other embodiments may also have an additional lumen (not shown) disposed in a portion of electrode array 144 configured to remain outside cochlea 115 near cochleostomy region 152 into which a drug release capsule component which promotes tissue growth may be inserted. Other drug release capsule components in the same embodiment may be inserted inside cochlea 115 in lumen 224 to provide other therapeutic benefits such as promoting enhanced stimulation. Although the components of drug release capsule 202 are described above as being separate from one other, it is to be understood that in other embodiments, the various drug release components carrying different types of drugs may be joined or produced as a unitary body which is inserted into lumen 224.

In other embodiments, various drug release capsule components may be inserted in lumen 224 together and in a specific sequence so as to direct the various drugs being carried by one or more of those drug release capsule components to different locations within cochlea 115. For example, a component carrying a stimulation enhancing drug may be inserted into lumen 224 prior to a component carrying a tissue growth promoting drug so that each drug may be directed to deeper regions in cochlea 115 or to cochleostomy region 152, respectively, to provide the various therapeutic benefits afforded by each component. Intermediate to inserting each component into lumen 224, one or more inert or other component not carrying any drugs may be inserted, to provide one or more spaces between components carrying drugs. Furthermore, one or more of these inert or other components may provide a sealing function, in order to segregate fluids, drugs and other materials from passing the sealing component in lumen 224. The sealing components may be manufactured of a hygroscopic material which swells soon after being exposed to liquid so as to provide a seal inside lumen 224 thereby segregating the inner regions of lumen 224 from the portion outside the seal inside lumen 224. In other embodiments, a shape memory polymer material may be used to manufacture a seal component.

FIG. 3A is a partial perspective view of cochlea 115 (FIG. 1) and an embodiment of electrode assembly 140 of cochlear implant 120 (FIG. 1). As noted, in this exemplary embodiment, electrode carrier member 220 has a lumen 224 with multiple portholes 206 disposed therein.

FIG. 3B is the same perspective view of cochlea 115 and electrode assembly 140 as shown in FIG. 3A, with drug release capsule 300 positioned in lumen 224 of carrier member 220.

FIG. 3C is an enlarged cross-sectional view of a portion of cochlea 115 and electrode assembly 140.

Similarly, in the exemplary application of a cochlear implant in which the implanted component that implements embodiments of the drug release system is a fully implanted component, it should be appreciated that the present invention may be implemented in implanted medical device components that are partially implanted. These alternative embodiments and applications of the present invention are described in greater detail below.

Further features and advantages of the present invention are described in U.S. patent application Ser. No. 10/416,634, filed on Nov. 10, 2003, entitled "Apparatus For Delivery of Pharmaceuticals To The Cochlear", which is a National Phase Application of International Application No. PCT/AU01/01479, filed Nov. 14, 2001, entitled "Apparatus For Delivery of Pharmaceuticals To The Cochlear", which claims priority from Australian Provisional Application No. PR 1484, filed Nov. 14, 2000. This application also claims priority from U.S. Provisional Patent Application No. 60/978,572, filed Oct. 9, 2007, entitled "Drug release Capsule For Implantation Into An Accessible Lumen Of An Implanted Medical Device. The above applications are hereby incorporated by reference herein.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. An implantable component of a cochlear implant comprising:
    a carrier member comprising a plurality of electrodes disposed along said carrier member and, said carrier member having an accessible lumen and one or more drug release ports fluidically coupling the lumen with an exterior environment of the implanted component; and
a drug-delivery capsule that carries at least one drug and is configured to release the at least one drug,
wherein the capsule and lumen are correspondingly configured such that the capsule may be securely retained within the lumen and the capsule may be introduced into the lumen so that when the drug-delivery capsule releases the at least one drug, the at least one drug may travel through the lumen and exit the implantable component via at least one of the one or more drug release ports.

2. The implantable component of claim 1, wherein the capsule and lumen are further correspondingly configured such that the capsule may be advanced to a desired position in the lumen.

3. The implantable component of claim 1, wherein said one or more drug release ports are dimensioned and arranged such that at least one of rate and quantity of the one or more drugs released by said capsule is controlled thereby.

4. The implantable component of claim 3, wherein a first group of said one or more drug release ports has a first dimension that is not equal to a second dimension of a second group of said one or more drug release ports.

5. The implantable component of claim 3, wherein said lumen is configured to secure the drug-delivery capsule in a first location in the lumen, and wherein said one or more drug release ports disposed closer to the first location are smaller than said one or more drug release ports disposed further from the first location.

6. The implantable component of claim 2, further comprising one or more tabs coupled to a wall of the lumen, wherein the one or more tabs retains the capsule at a desired position in the lumen.

7. The implantable component of claim 6, wherein the one or more tabs are malleable such that the capsule may travel past the one or more tabs when a force is applied to the capsule.

8. The implantable component of claim 1, wherein two or more drug release ports are disposed circumferentially around said lumen.

9. A drug delivery system comprising:
an implanted component having an accessible lumen and one or more drug release ports fluidically coupling the lumen with an exterior environment of the implanted component, wherein a first group of said one or more drug release ports has a first dimension, and wherein a second group of said one or more drug release ports has a second dimension not equal to the first dimension; and
a drug-delivery capsule that carries at least one drug and may be introduced into the lumen so that when the drug-delivery capsule releases the at least one drug, the at least one drug may travel through the lumen and exit the implantable component via at least one of the one or more drug release ports,
wherein said one or more drug release ports are configured such that at least one of rate and quantity of the one or more drugs released by said capsule is controlled thereby, and
wherein the capsule and lumen are further correspondingly configured such that the capsule may be securely retained within the lumen.

10. The drug delivery system of claim 9, wherein the capsule and lumen are further correspondingly configured such that the capsule may be advanced to a desired position in the lumen.

11. The drug delivery system of claim 9, wherein said drug delivery system is an implantable hearing prosthesis.

12. The drug delivery system of claim 11, wherein said implantable hearing prosthesis is a cochlear implant.

13. The drug delivery system of claim 9, wherein said implantable component is a cochlear implant carrier member comprising a plurality of electrodes disposed along said carrier member.

14. The drug delivery system of claim 9, wherein said one or more drug release ports are disposed circumferentially around said lumen.

15. The implantable component of claim 10, further comprising one or more tabs coupled to a wall of the lumen, wherein the one or more tabs retains the capsule at a desired position in the lumen.

16. The implantable component of claim 15, wherein the one or more tabs are malleable such that the capsule may travel past the one or more tabs when a force is applied to the capsule.

17. The implantable component of claim 9, wherein two or more drug release ports are disposed circumferentially around said lumen.

18. A drug delivery system comprising:
an implanted component having an accessible lumen and one or more drug release ports fluidically coupling the lumen with an exterior environment of the implanted component; and
a drug-delivery capsule that carries at least one drug and is configured to release the at least one drug,
wherein the capsule and lumen are correspondingly configured such that the capsule may be introduced into the lumen so that when the drug-delivery capsule releases the at least one drug, the at least one drug may travel through the lumen and exit the implantable component via at least one of the one or more drug release ports,
wherein said one or more drug release ports are configured such that at least one of rate and quantity of the one or more drugs released by said capsule is controlled thereby, and
wherein said lumen is configured to secure the drug-delivery capsule in a first location in the lumen, and wherein at least one of said one or more drug release ports disposed closer to the first location is smaller than at least one of said one or more drug release ports disposed further from the first location.

19. The drug delivery system of claim 18, wherein the capsule and lumen are further correspondingly configured such that the capsule may be advanced to a desired position in the lumen.

20. The drug delivery system of claim 18, wherein the capsule and lumen are further correspondingly configured such that the capsule may be securely retained within the lumen.

21. The drug delivery system of claim 18, wherein said drug delivery system is an implantable hearing prosthesis.

22. The drug delivery system of claim 21, wherein said implantable hearing prosthesis is a cochlear implant.

23. The drug delivery system of claim 18, wherein said implantable component is a cochlear implant carrier member comprising a plurality of electrodes disposed along said carrier member.

24. The drug delivery system of claim 18, wherein said one or more drug release ports are disposed circumferentially around said lumen.

25. The implantable component of claim 19, further comprising one or more tabs coupled to a wall of the lumen, wherein the one or more tabs retains the capsule at a desired position in the lumen.

26. The implantable component of claim 25, wherein the one or more tabs are malleable such that the capsule may travel past the one or more tabs when a force is applied to the capsule.

\* \* \* \* \*